United States Patent [19]

Barben, II

[11] Patent Number: 4,682,113

[45] Date of Patent: Jul. 21, 1987

[54] PURE WATER CONDUCTIVITY SENSOR

[75] Inventor: Theodore R. Barben, II, Carson City, Nev.

[73] Assignee: TBI, Carson City, Nev.

[21] Appl. No.: 804,217

[22] Filed: Dec. 3, 1985

[51] Int. Cl.$^4$ ............................................. G01R 27/22
[52] U.S. Cl. .................................... 324/441; 324/439;
210/900; 204/406
[58] Field of Search ............... 324/438, 439, 441, 443;
204/406; 203/3, 2; 210/900, 742, 746, 85

[56] References Cited

U.S. PATENT DOCUMENTS 4,118,663 10/1978 Barben, II ............................. 324/443
4,303,887 12/1981 Hill et al. ............................. 324/441
4,587,518 5/1986 King .................................... 324/441 X Primary Examiner—Reinhard J. Eisenzopf
Assistant Examiner—Robert W. Mueller
Attorney, Agent, or Firm—Nilsson, Robbins, Dalgarn, Berliner, Carson & Wurst

[57] ABSTRACT

A multiple electrode conductivity sensor generates an output to be applied to a special temperature compensation system that responds to a temperature sensor signal indicative of the sample water temperature. The temperature signal selectively operates a memory unit that contains separate water and salt correction values to be used in adjusting the measured conductivity output. The water correction value represents the conductivity of absolutely pure water at the measured temperature, and this value can be subtracted from the measured total conductivity to produce a conductivity value attributable only to salt impurities. The salt correction signal from the memory unit is then used to scale the measured salt conductivity signal at the standard reference temperature of 25° C., thereby achieving a corrected salt conductivity measurement that can be added to a fixed pure water correction signal representative of the conductivity of pure water at that temperature. The sum of these values yields an adjusted output signal that accurately reflects the conductivity (or resistivity) of the pure water solution at the standard 25° C. temperature.

10 Claims, 2 Drawing Figures

PURE WATER CONDUCTIVITY SENSOR

A multiple electrode conductivity sensor generates an output to be applied to a special temperature compensation system that responds to a temperature sensor signal indicative of the sample water temperature. The temperature signal selectively operates a memory unit that contains separate water and salt correction values to be used in adjusting the measured conductivity output. The water correction value represents the conductivity of absolutely pure water at the measured temperature, and this value can be subtracted from the measured total conductivity to produce a conductivity value attributable only to salt impurities. The salt correction signal from the memory unit is then used to scale the measured salt conductivity signal at the standard reference temperature of 25° C., thereby achieving a corrected salt conductivity measurement that can be added to a fixed pure water correction signal representative of the conductivity of pure water at that temperature. The sum of these values yields an adjusted output signal that accurately reflects the conductivity (or resistivity) of the pure water solution at the standard 25° C. temperature.

To avoid inaccuracies due to electrode deposits, the excitation voltage applied across the current electrodes of a four electrode conductivity sensor is monitored to produce a warning whenever the sensor circuitry nears the limit of its ability to overcome the effect of accumulated deposits, thus alerting the operator to the need for cleaning the electrodes before substantial inaccuracies can occur.

BACKGROUND OF THE INVENTION

In recent years, increasing use has been made of very high purity water in various applications such as the production of semiconductors for solid state electronics, as feed water for nuclear power generators, and in ultratrace analysis. Operators of such systems must be continually alert to the presence of impurities that can impair their operations or product. One of the most useful methods of accomplishing this purpose lies in the monitoring of solution conductivity (or its inverse, resistivity) to indicate the presence of ions in the water. Although conductivity is not specific in identifying the type of impurities present, it is still most useful in many applications since high purity water requires the absence of almost anything conductive, and can actually serve as a valuable backup in assuring proper pH that is notoriously difficult to measure in such systems.

Various instruments are available for measuring conductivity (or its reciprocal value, resistivity) at normal conductivity levels. However, attempts to adapt these prior instruments to measurements of the extremely low conductivity levels encountered in very pure water have not been entirely successful. The main problem lies in the fact that impurities are not the only sources of ions in water. Very small quantities of the water itself break up or disassociate to form hydrogen and hydroxyl ions which are highly conductive. Such minute quantities of water ions are not significant at higher conductivity levels since they contribute little to the overall conductivity. But in high purity water, where conductivity in the range of one micromho per centimeter or less occurs, water ions become the dominant source of conductivity. To further complicate matters, the effects of temperature changes on water ion conductivity happens to be about three times that produced by temperature variations on salt solutions, such as sodium chloride, which is the most common impurity found in pure water systems. Thus, to achieve accuracy, the conductivity measurements must be temperature compensated for the low level salt concentrations at one rate, whereas the water ions require another.

A straightforward technique for achieving temperature compensation for pure water conductivity measurements involves generating a signal value representative of the conductivity of pure water at the measured temperature, and then subtracting this pure water value from the total conductivity being measured by the precision conductivity meter. The remainder leaves a conductivity value representative of that contributed only by the salt ions, which can then be converted to a signal representative of the conductivity for salts at the standard 25° C. temperature. The temperature corrected signal for the salt conductivity can then be added to a fixed value representing pure water conductivity at the standard reference temperature to yield an accurate overall conductivity measurement. However, in subtracting the pure water value from the measured conductivity figure, the effect of any error in the measured conductivity is greatly amplified due to the fact that the pure water conductivity generally represents a substantial portion of the total conductivity. It thus becomes extremely important to avoid measurement errors such as those due to deposits on the electrodes of the conductivity meter probe which is immersed in the pure water sample.

The four electrode conductivity sensor described in this applicant's prior U.S. Pat. No. 4,118,663 issued Oct. 3, 1978, and assigned to the same assignee as the present invention, effectively avoids errors in measuring conductivity due to fouling of the electrodes due to buildup of impurities or oxidation products on the electrode surfaces. In the case of very low conductivity levels encountered in pure water, the need to avoid such errors due to such electrode deposits becomes crucial because such errors can represent a substantial proportion of the total conductivity signal. In the patented four electrode system, the voltage applied to two electrodes from an operational amplifier circuit is automatically adjusted to compensate for voltage drops resulting from electrode deposits. But, as the voltage increases beyond a predetermined level, the system reaches the limit of its ability to compensate for these deposits and the electrodes must then be cleaned to avoid errors.

SUMMARY OF THE INVENTION

Total conductivity of pure water can be measured using conventional conductivity sensor instruments, preferably of the four electrode variety, that produce an output signal proportional to the total conductivity. A conventional temperature sensor supplies an output signal indicative of the water temperature to be used in generating two separate temperature dependent values for compensating the total conductivity signal from the conductivity sensor. The first temperature value generated corresponds to the conductivity of theoretically pure water at the measured temperature, and this value is subtracted from the total conductivity sensor output to produce a net conductivity value corresponding to that portion of the total conductivity attributable to salt impurities alone. The second temperature compensating value selected in accordance with the measured water temperature represents the scaling factor by which the salt conductivity changes due to the difference between the measured temperature and the standard reference temperature of 25° C. This temperature scaling factor is applied to a variable gain amplifier to control the amplification of the net conductivity signal previously obtained by subtracting the pure water value at the measured temperature from the uncorrected output of the conductivity sensor. The corrected amplifier output thus represents the conductivity of the salt normalized to the standard 25° C. reference temperature, which can then be applied to a summation circuit to be combined with a fixed signal value indicative of the conductivity of theoretically pure water at that same temperature. The output of the summation circuit thus constitutes an accurate measure of the total sample conductivity corrected to the standard reference temperature of 25° C.

To avoid appreciable errors in the conductivity sensor output due to electrode deposits, the voltage output from the operational amplifiers used to maintain a constant excitation voltage between the current electrodes at the solution interface is monitored to determine when it exceeds a predetermined level in compensating for voltage drops due to deposit buildups on these electrodes. When this happens, an alarm or indicator is actuated to alert the operator that the electrodes need cleaning.

DETAILED DESCRIPTION

Figure 1:
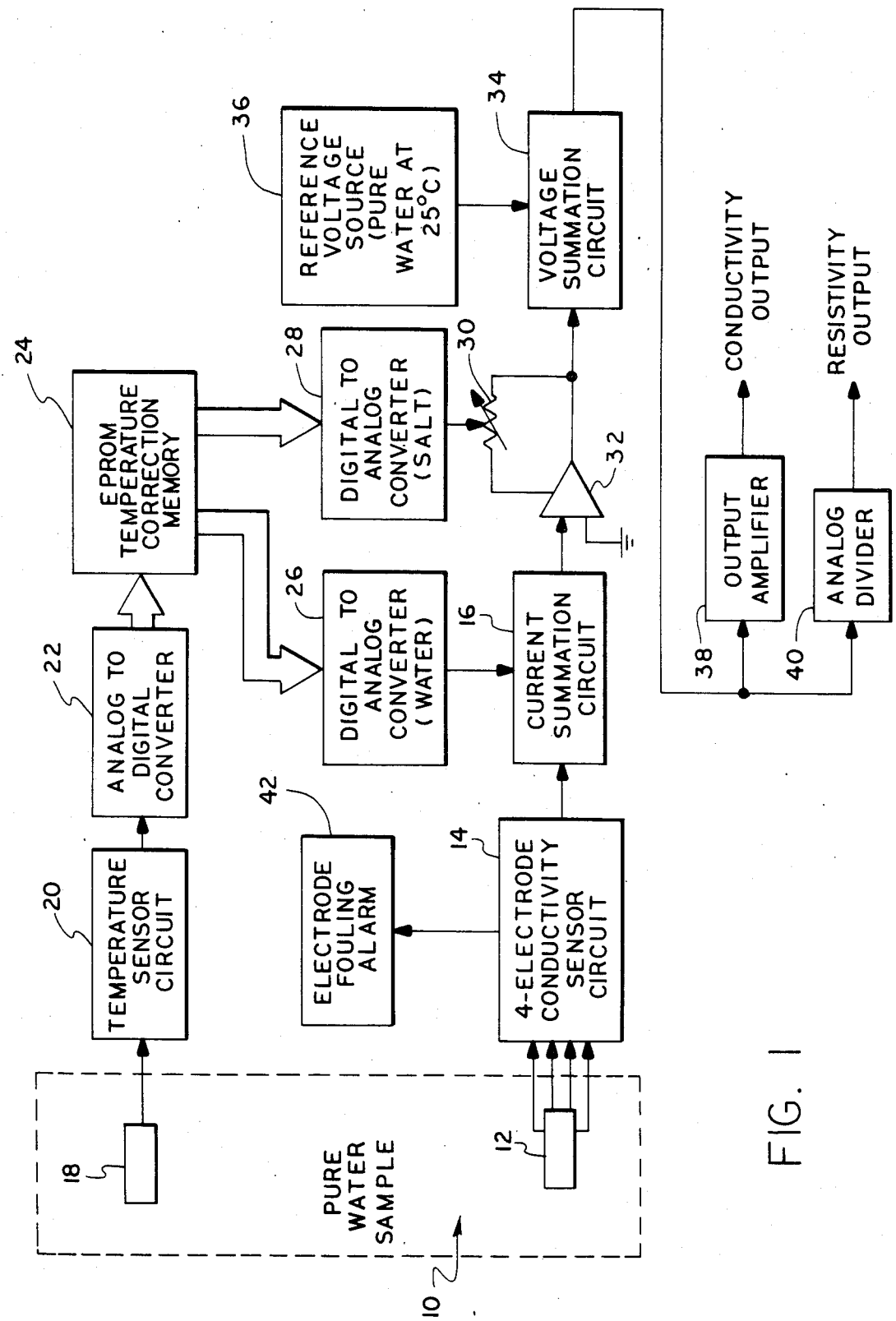
FIG. 1 is a generalized schematic circuit diagram in block diagram form illustrating the preferred form of the pure water conductivity measuring system in accordance with this invention.

Referring now to FIG. 1, which contains a generalized circuit schematic of the pure water conductivity sensor in accordance with this invention, a pure water sample or stream has a multiple electrode probe 12 immersed in it and connected to an appropriate conductivity sensor circuit 14. While other types of water conductivity measuring instruments might be employed, the preferred system in accordance with this invention employs the four electrode probe 12 and associated conductivity sensor circuit 14 corresponding to that described and illustrated in this inventor's previous U.S. Pat. No. 4,118,663 issued Oct. 3, 1978 and assigned to the same assignee as the present invention. An output signal indicative of the total conductivity of the pure water sample 10 is supplied by the conductivity sensor circuit 14 to one input of a summation circuit 16.

Also immersed in the pure water sample 10 is a temperature probe 18 connected to a temperature sensor circuit 20 that produces a temperature output signal indicative of the measured water temperature. Preferably the temperature sensor circuit 20 output can be selected to produce a direct current proportional to the Kelvin temperature in the range between 0° C. and 100° C. that, for example, varies at one microampere per degree, so that the output signal will vary from 273 microamperes to 373 microamperes over this range. That temperature output signal can then be applied to an analog-to-digital (A/D) converter 22 to generate a multibit digital word corresponding to a selected memory address position within a digital memory 24. The digital memory 24 may typically be an erasable programmable read-only memory (EPROM) that receives a nine bit digital word from the A/D converter 22 and wherein each address location contains two separate six bit bytes making up a twelve bit word. Upon receiving the memory address signal from the A/D converter 22, the two digital words are readout from the selected memory address position to a respective one of a pair output digital to analog (D/A) converters 26 and 28. The digital value applied to the first D/A converter 26 produces a direct current output proportional to the conductivity of pure water at the measured temperature, which output is then subtracted from the total conductivity output from the conductivity sensor circuit 14. Preferably, the direct current output from the conductivity sensor circuit 14 is applied to the summation circuit 16 to be combined with the direct current of opposite polarity from the digital analog converter 26 to produce a difference signal output corresponding to the conductivity level of salt in the sample at the measured temperature.

The digital values representing the conductivity of pure water contained in the digital memory 24 are those available from an article entitled "Temperature Dependence and Measurement of Resistivity of Pure Water" by Truman S. Light published in the June 1984 issue of the periodical "Analytical Chemistry", Volume 56, No. 7 at pp. 138–142. These values can also be closely approximated through use of the empirical equation described in that article and in a similar article entitled "Measurement of Conductivity in High Purity Water" by Robert C. Hunt published in the July/August 1985 issue of the periodical "Ultra Pure Water". These articles also reveal another problem encountered in measuring conductivity of pure water that results from an apparent anomaly in that absolutely pure water does not exhibit minimum conductivity; instead, minimum conductivity occurs in water containing very small impurity concentrations equivalent to 0.8 parts per billion of sodium hydroxide, as noted in the T. S. Light article.

The other digital word readout from the selected address location within the temperature collection memory 24, as determined by the temperature sensor output, is applied to another digital to analog converter 28 that produces an analog output signal to control the resistance value of a variable feedback resistor 30 that determines the degree of amplification provided by a variable gain amplifier 32, which receives the output signal from the summation circuit 16. The amplifier input is thus indicative of that portion of the total conductivity signal attributable to the salt at the measured water temperature since the conductivity value representing pure water has already been subtracted. The temperature correction signal applied from the memory 24 through the digital analog converter 28 operates to scale the output of the variable gain amplifier 32 to a level representative of the measured salt conductivity to the standard reference temperature of 25° C. Preferably, this corrected salt conductivity signal varies between 0 and 10 volts direct current, and correspond to conductivity values between 0 to 2 micromhos, to be applied as one input to another voltage summation circuit 34. The corrected salt conductivity output from the amplifier 32 is added to a fixed reference voltage level of 0.274 volts generated from a regulated voltage source 36. That value of 0.274 volts corresponds to the theoretical conductivity of pure water at 25° C. so that the output from the voltage summation circuit 34 represents the measured conductivity of the pure water sample 10 corrected to the standard reference temperature of 25° C. The combined value may then be applied as the input to a non-inverting output amplifier 38 to produce an output proportional to the measured conductivity, or it can be applied through an inverting analog divider 40 to produce a signal on an appropriate voltage scale indicative of the sample resistivity, typically on a scale from 0 to 20 megohms.

In performing these operations, the fact that the pure water conductivity value from the digital analog converter 26 constitutes a substantial portion of the total conductivity value measured by the sensor circuit 14 has the effect of magnifying any error encountered in measuring the total conductivity. For example, errors amounting to only 3% in the total measured conductivity can result in errors of as much as 10% in the temperature compensated value. This is demonstrated using typical values that might well be encountered in actual practice. Using a typical low level sodium chloride concentration of only 1 part per billion (ppb), the true total conductivity measured by the conductivity sensor 14 at 75° C. would be 0.3953 micromhos. At that temperature, the conductivity attributable to pure water would be 0.3906 micromhos, making a difference of 0.0047 micromhos that is represented by the output from the current summation circuit 16 after subtraction of the pure water conductivity value from the digital analog converter 26. However, with only a 3% error in the measured conductivity, the total conductivity value would be 0.4072 micromhos, instead of the 0.3953 value, which means the difference output from the current summation circuit 16 would be almost four times larger, specifically 0.0166 micromhos. In scaling this amount to the 25° C. standard reference temperature, the input to the variable gain amplifier 32 would be divided by the factor 2.20, yielding an erroneous output value of 0.0075 micromhos as against a true value of only 0.0021. After adding back the theoretical pure water conductivity at 25° C., which is 0.0548 micromhos, the total corrected conductivity value as measured would be 0.0623 as compared with the true value of 0.0568. The difference between these values represents an error in total measured conductivity of 9.8%. It thus seems quite important to avoid sources of measurement error such as that encountered due to electrode fouling or deposits over long time periods.

Figure 2:
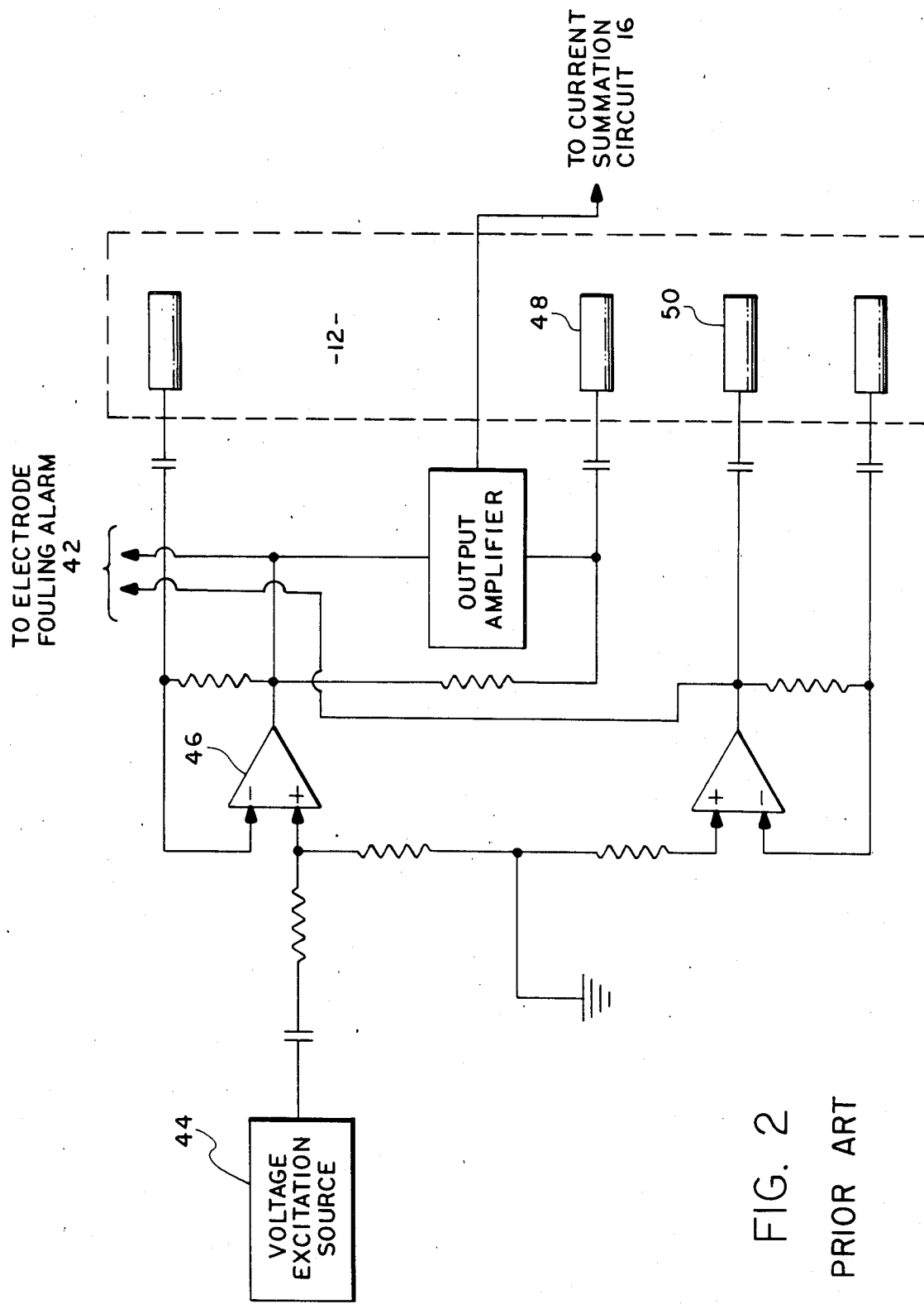
FIG. 2 is a more detailed generalized circuit diagram illustrating the principal elements of a four electrode conductivity sensor system adapted to monitor the condition of the electrodes.

In the system of the present invention, errors due to electrode deposits are avoided through use of the previously described four electrode conductivity sensor of the type illustrated and described in the U.S. Pat. No. 4,118,663. As illustrated in FIG. 2, which schematically illustrates one preferred embodiment of the previously patented conductivity sensor circuit, an alternating current excitation, as illustrated in the patent FIG. 2, is preferable. In this case, the voltage output from one of the operational amplifiers used to maintain the fixed excitation voltage between the current electrodes is monitored to actuate an electrode fouling alarm 42 that warns the operator that the electrodes need cleaning. In this particular version, an alternating voltage excitation source 44 is employed to avoid polarization or buildup of oxidation products on the electrodes when a DC current is applied, as described in the previous patent. The regulated output voltage is applied as a fixed input to the positive input terminal of the operational amplifier 46 that varies its output voltage to maintain the voltage at a constant level at the water interface between the current electrodes 48 and 50. As deposits on the electrodes build up, the voltage drop from each electrode itself to the interface with the water sample increases, so the output level of the operational amplifier 46 must be increased to maintain the voltage between the current electrodes 48 and 50 constant at the water interface. When that output voltage from the operational amplifier 46 reaches a predetermined level where the circuit approaches the limit of its ability to adjust for the effect of these deposits, an electrode fouling alarm 42 is triggered to actuate a warning light or the like alerting the operator to the need for cleaning the electrodes.

Of course it should be understood that, where a specific component and circuitry arrangements have been illustrated and described herein in order to indicate a preferred embodiment of the invention, it should be understood that various other components and arrangements may be employed without departing from the spirit and scope of the invention as defined in the appended claims.

What is claimed is:

1. A system for measuring conductivity of a high purity water sample comprising:
    a total conductivity measuring means having a multiple electrode probe immersed in said sample for generating a total conductivity signal proportional to the total conductivity of the sample;
    a temperature sensing means for generating a temperature output indicative of the temperature of the sample;
    first compensation means responsive to the temperature output from the temperature sensing means for generating a pure water correction signal corresponding to the conductivity of absolutely pure water at the temperature of the sample;
    first summation means for subtracting the pure water correction signal generated by the first compensation means from the total conductivity signal generated by the conductivity measuring means to produce a net conductivity signal indicative of the conductivity value of salt impurities in the sample;
    second compensation means for generating a salt correction signal corresponding to the ratio between the conductivity of the salt at the measured temperature as compared with a standard reference temperature;
    amplifier means responsive to the salt correction signal for adjusting the net conductivity signal applied to its input to produce an adjusted salt conductivity output proportional to the conductivity of the salt at a standard reference temperature;
    second summation means for adding the adjusted salt conductivity output to a fixed amplitude signal, which corresponds to the conductivity of absolutely pure water at the standard reference temperature, to produce a combined output signal corresponding to the total conductivity of the sample being measured at the standard reference temperature.

2. The pure water conductivity system of claim 1 wherein:
    said first and second compensation means both consist of a digital memory means for receiving a memory address signal indicative of the measured temperature of the sample to produce separate digital outputs corresponding to the value of said pure water correction and of said salt correction signals to be applied through respective digital to analog converters to generate direct current analog signals to be applied to said first summation circuit and to said amplifier means; and said conductivity measuring means generates an analog total conductivity signal of a polarity opposite to the polarity of the analog pure water correction signal to be combined in said first summation circuit to produce said net conductivity output.

3. The pure water conductivity measuring system of claim 2 wherein:

said amplifier means constitutes a variable gain amplifier having a variable feedback impedance element responsive to the analog salt correction signal to vary the amplifier gain in accordance with the amplitude of the salt correction signal.

4. The pure water conductivity measuring system of claim 3 wherein:

said conductivity measuring means comprises a four electrode conductivity measuring instrument having separate current and voltage electrode pairs coupled to an operational amplifier circuit that maintains a current flow at a given amplitude and a voltage with an amplitude between the current electrodes at the interface with the sample at a constant fixed voltage so that the amplitude of the current flow between the current electrodes is directly proportional to the total conductivity.

5. The pure water conductivity measuring system of claim 4 further comprising:

an electrode fouling alarm responsive to the amplitude of the voltage applied to said current electrodes from said operational amplifier circuit for activating an alarm means whenever said voltage amplitude exceeds a predetermined level to alert an operator to a need for cleaning the electrodes.

6. The pure water conductivity measuring system of claim 1 wherein:

said conductivity measuring means comprises a four electrode conductivity measuring instrument having separate current and voltage electrode pairs coupled to an operational amplifier circuit that maintains a current flow at a given amplitude and a voltage with an amplitude between the current electrodes at the interface with the sample at a constant fixed voltage so that the amplitude of the current flow between the current electrodes is directly proportional to the total conductivity.

7. The pure water conductivity measuring system of claim 6 further comprising:

an electrode fouling alarm responsive to the amplitude of the voltage applied to said current electrodes from said operational amplifier circuit for activating an alarm means whenever said voltage amplitude exceeds a predetermined level to alert an operator to a need for cleaning the electrodes.

8. A system for measuring conductivity of a high purity water sample comprising:

a four electrode conductivity sensor for generating a total conductivity signal proportional to the total conductivity of the sample;

a temperature sensing means for generating a temperature output indicative of the temperature of the sample;

first compensation means responsive to the temperature output from the temperature sensing means for subtracting from said total conductivity a signal value corresponding to the conductivity of absolutely pure water at the sample temperature to produce a net conductivity signal;

second compensation means responsive to said temperature output for selectively amplifying said net conductivity signal to produce an adjusted output proportional to the conductivity of salt at a standard reference temperature; and summation means for summing the adjusted conductivity output for a fixed amplitude signal that corresponds to the conductivity of absolutely pure water at the standard reference temperature to produce a combined output signal corresponding to the total conductivity of the sample at said standard reference temperature.

9. The pure water conductivity measuring system of claim 8 wherein:

said four electrode conductivity sensor has separate current and voltage electrode pairs coupled to an operational amplifier circuit that maintains a current flow at a given amplitude and a voltage between the current electrodes at the interface with the sample at a constant fixed voltage with an amplitude so that the amplitude of the current flow between the current electrodes is directly proportional to the total conductivity.

10. The pure water conductivity measuring system of claim 9 further comprising:

an electrode fouling alarm responsive to the amplitude of the voltage applied to said current electrodes from said operational amplifier circuit for giving an alarm whenever said voltage amplitude exceeds a predetermined level to alert an operator to a need for cleaning the electrodes.

* * * * *